United States Patent
Thomson et al.

(10) Patent No.: US 7,220,584 B2
(45) Date of Patent: *May 22, 2007

(54) METHOD OF MAKING EMBRYOID BODIES FROM PRIMATE EMBRYONIC STEM CELLS

(75) Inventors: James A Thomson, Madison, WI (US); Vivienne S. Marshall, Madison, WI (US); Jennifer J. Swiergiel, Roscoe, IL (US)

(73) Assignee: Wisconsin Alumni Research Foundation, Madison, WI (US)

( * ) Notice: Subject to any disclaimer, the term of this patent is extended or adjusted under 35 U.S.C. 154(b) by 368 days.

This patent is subject to a terminal disclaimer.

(21) Appl. No.: 10/632,399

(22) Filed: Aug. 1, 2003

(65) Prior Publication Data

US 2004/0023376 A1 Feb. 5, 2004

Related U.S. Application Data

(63) Continuation of application No. 09/510,444, filed on Feb. 21, 2000, now Pat. No. 6,602,711.

(51) Int. Cl.
*C12N 5/02* (2006.01)
*C12N 5/04* (2006.01)
*C12N 5/08* (2006.01)
*A01N 1/02* (2006.01)

(52) U.S. Cl. .................. 435/377; 435/1.1; 435/325; 435/363; 435/375

(58) Field of Classification Search ................. 435/1.1, 435/325, 363, 375, 377
See application file for complete search history.

(56) References Cited

U.S. PATENT DOCUMENTS 6,602,711 B1 * 8/2003 Thomson et al. ........... 435/378

* cited by examiner

*Primary Examiner*—Deborah Crouch
(74) *Attorney, Agent, or Firm*—Quarles & Brady LLP

(57) ABSTRACT

Primate embryoid bodies are formed from primate ES cells. The ES cells form clumps. One then removes the clumps, as clumps, and permits incubation under non-adherent conditions. The development of embryoid bodies from primate ES cells is dependent on maintaining the aggregation of cells, as individualized cells will rapidly die.

10 Claims, No Drawings

METHOD OF MAKING EMBRYOID BODIES FROM PRIMATE EMBRYONIC STEM CELLS

CROSS REFERENCES TO RELATED APPLICATIONS

This application is a continuation of application Ser. No. 09/510,444, filed Feb. 21, 2000 now U.S. Pat. No. 6,602,711.

STATEMENT REGARDING FEDERALLY SPONSORED RESEARCH

The work with the non-human primate cells described below was supported by a grant with United States government support awarded by the following agency: NIH RR11571. The United States has certain rights in this invention. No U.S. government funds were used for the work with human cells described herein.

BACKGROUND OF THE INVENTION

Undifferentiated primate embryonic stem ("ES") cells can be cultured indefinitely and yet maintain the potential to form differentiated cells of the body. See U.S. Pat. No. 5,843,780; J. Thomson, et al., 282 Science 1145–1147 (1998); and J. Thomson, et al., 38 Biology 133–165 (1998). The disclosure of these publications and of all other publications referred to herein are incorporated by reference as if fully set forth herein.

Primate ES cells thus provide an exciting new model for understanding the differentiation and function of human tissue, and offer new strategies for drug discovery and testing. They also promise new therapies based on the transplantation of ES cell-derived tissues. For example, human and rhesus monkey ES cells injected into immunocompromised mice form benign teratomas with advanced differentiated derivatives representing all three embryonic germ layers. Easily identified differentiated cells in human ES cell teratomas include smooth muscle, striated muscle, bone, cartilage, gut and respiratory epithelium, keratinizing squamous epithelium, hair, neural epithelium, and ganglia.

Human and non-human primate ES cell lines provide a particularly powerful new model for understanding normal human development and thus also for understanding abnormal human development. Because of the potential risk to the resulting child, experimental manipulation of the post-implantation human embryo is ethically unacceptable and as a result functional studies on human embryos are lacking. Consequently, what is known about human development in the early post-implantation period is based almost entirely on static histological sections of a few human embryos and on analogy to experimental embryology studies of the mouse.

However, early mouse and primate development differ significantly. For example, human and mouse embryos differ in the timing of embryonic genome expression, in the formation, structure, and function of the fetal membranes and placenta and in the formation of an embryonic disc instead of an egg cylinder. The earliest events of human development are critically involved in human infertility, pregnancy loss, and birth defects. Primate ES cells offer a new window for understanding these early human developmental events and for understanding the pathogenesis of developmental failures.

Primate ES cells also provide a potentially unlimited source of differentiated, euploid, non-transformed cells for investigators interested in the normal function and pathology of specific differentiated primate cells. Such purified populations of specific ES cell-derived cells will also likely be useful for drug discovery, toxicity screens, and will provide a source of cells for transplantation.

For tissues such as the heart that completely lack a tissue-specific stem cell, primate ES cells will prove even more valuable. Primate ES cells also offer the promise of new transplantation therapies. When disease results from the destruction or dysfunction of a limited number of cell types, such as in Parkinson's disease (dopaminergic neurons), or juvenile onset diabetes mellitus (pancreatic β-islet cells), the replacement of those specific cell types by ES cell derivatives could offer potentially life long treatment.

To accomplish these goals, it is desirable to more efficiently differentiate ES cells to specific lineages. Considerable progress in causing non-primate ES cell differentiation to neural, hematopoietic, and cardiac tissue has been made. See e.g. T. Doetschman, et al., 87 J. Embry. And Exper. Morph. 27–45 (1985); G. Keller, 7 Current Op. In Cell Biol. 862–869 (1995); U.S. Pat. No. 5,914,268. In each of these examples, ES cells were first formed into "embryoid bodies", three-dimensional ES cell aggregates that facilitate subsequent differentiation.

However, analogous experiments on primate ES cells demonstrated that embryoid body formation by conventional murine protocols fail. In such conventional protocols ES cells are dispersed to single cells, and either allowed to aggregate into embryoid bodies under conditions that prevent cell attachment to the substrate, or the ES cells are allowed to grow into embryoid bodies from single cells or clusters suspended in methylcellulose. We have learned that primate ES cells die rapidly when dispersed to single cells if attachment is prevented, so they do not successfully aggregate, and they therefore do not grow out from clones in methylcellulose.

It can therefore be seen that a need exists for improved methods for producing primate embryoid bodies, and differentiated cells derived therefrom.

BRIEF SUMMARY OF THE INVENTION

The present invention provides a method for producing primate embryoid bodies from colonies of primate embryonic stem cells that are adhering to a substrate. One removes the adhering colonies of the embryonic stem cells from the substrate in clumps. One then incubates the clumps in a container under conditions in which the clumps are essentially inhibited from attaching to the container and coalesce into embryoid bodies. For purposes of this application, a clump is a grouping of two or more stem cells, preferably a clump large enough to be visible to the naked eye.

In one preferred form the removal step is in the presence of an agent that promotes disassociation of the clumps from the substrate as clumps. A purely chemical agent such as Versene® calcium disodium EDTA chelating agent can be used. However, more preferred is a proteinase that preferentially acts on the extra cellular matrix such as dispase, collagenase, catalase, neuraminidase, pancreatin, pancreatic elastase or trypsin. If trypsin is used the removal step must be conducted quickly and at relatively low concentrations in order to prevent the trypsin from also destroying the clumps. Enzyme EDTA mixes can also be used to advantage.

In another form the removal step involves mechanically scraping the clumps from the substrate as clumps.

In another aspect the incubation step can be conducted by agitating the container (e.g. by gently rocking, shaking, or vibrating it), the container for the incubation step can be a non-attaching bacterial grade culture plastic, and/or the incubation step can be in the presence of a serum-free medium which lacks serum attachment factors.

In another aspect the invention provides primate embryoid bodies that have been derived (directly or indirectly) using the above methods.

In still another aspect the invention provides differentiated cells derived (directly or indirectly) from the embryoid bodies.

In accordance with the present invention, primate ES cells that have been cultured under standard conditions (see e.g. U.S. Pat. No. 5,843,780) are permitted to overgrow, pile up and/or otherwise closely associate in clumps on a substrate (e.g. a plastic tissue culture plate with standard feeder layer). They are then removed as clumps from the substrate (e.g. by incubating the colonies with an enzyme which attacks the ES cell colony's attachment to the substrate more strongly than ES cell attachments with ES cells). In such a case the enzyme could be dispase at a concentration of about 10 mg/ml.

Alternatively, the clumps could be removed as clumps by mechanically scraping with a micropipette, cell scraper, or the like.

The essentially intact colonies are then incubated under non-attaching conditions (preferably continuous rocking of the culture dish, culture on non-attaching bacterial grade culture plastic, and/or continuous culture in the presence of serum-free medium which lacks serum attachment factors). The colonies can then quickly coalesce into compact embryoid bodies, which can thereafter be allowed to differentiate either in continuous suspension, or after re-attachment to a substrate. Such embryoid bodies can be used to derive differentiated derivatives of endoderm, mesoderm, and ectoderm, and for obtaining other desired lineages.

It is an advantage of the present invention that it provides effective methods of forming primate embryoid bodies from primate embryonic stem cell lines. Another advantage of the present invention is to provide primate embryoid bodies suitable for differentiation into other primate cell types. Other features and advantages of the present invention will become apparent after study of the specification and claims which follow.

DETAILED DESCRIPTION OF THE PREFERRED EMBODIMENTS

Formation of Embryoid Bodies

Primate embryonic stem cells (e.g. rhesus or human—U.S. Pat. No. 5,843,780; J. Thomson, et al., 282 Science 1145–1147 (1998)) are cultured on mitotically inactivated (3000 rads g-radiation) mouse embryonic fibroblasts, prepared at $5 \times 10^4$ cells/cm$^2$ on tissue culture plastic previously treated by overnight incubation with 0.1% gelatin. E. Robertson, Embryo-derived Stem Cell Lines. In: Teratocarcinomas And Embryonic Stem Cells: A Practical Approach IRL Press: Washington, D.C., 71–112 (1987). Culture medium consists of 79% Dulbecco's modified Eagle medium (DMEM; 4500 mg of glucose per liter; without sodium pyruvate), 20% fetal bovine serum (FBS), 0.1 mM 2-mercaptoethanol, 1 mM L-glutamine and 1% nonessential amino acid stock (GIBCO).

One allows colonies to form clumps over a period of hours. ES cell colonies can then be removed from the tissue culture plate using physical or chemical methods that keep the ES cells in clumps.

For dispase or collagenase removal of ES cell colonies from the culture plate, the culture medium is removed from the ES cells. Dispase (10 mg/ml in ES culture medium) or collagenase (1 mg/ml solution in DMEM or other basal medium) is added to the culture plate. The culture plates are returned to the incubator for 10–15 minutes.

After dispase treatment the colonies can either be washed off the culture dishes or will become free of the tissue culture plate with gentle agitation. After collagenase treatment the cells can be scraped off the culture dish with a 5 ml glass pipette. Some dissociation of the colonies occurs, but this is not sufficient to individualize the cells. After chemical removal of the cells from the tissue culture plate, the cell suspension is centrifuged gently for 5 minutes, the supernatant is removed and discarded, the cells are rinsed, and the cells are resuspended in culture medium with or without serum.

Mechanical removal of the cells is achieved by using a pulled glass pipette to scrape the cells from the culture plate. Cell clumps can be immediately resuspended, without centrifugation, in fresh tissue culture medium.

Once colonies are removed from the tissue culture plate, the ES cells should remain in suspension during further embryoid body formation. This can be achieved by, for example, gently and continuously rocking the cell suspension. Cell suspensions are aliquoted into wells of 6-well tissue culture dishes, placed inside a sealed, humidified isolation chamber, gassed with 5% $CO_2$, 5% $O_2$ and 90% $N_2$ and placed on a rocker (Red Rocker, Hoefer Scientific Instruments). The rocker is housed inside an incubator maintained at 37° C. The culture plates can be rocked continuously for at least 48 hours and up to 14 days.

Every 2 days the plates are removed from the rocking device, the culture medium is removed, and fresh culture medium is added to the cells. The culture dishes are then returned to the rocking environment. Cells will also remain in suspension when cultured in suspension culture dishes (Nunc) without rocking, or when cultured in the absence of serum, which provides attachment factors. All cells must be cultured at 37° C., in a humidified, controlled gas atmosphere (either 5% $CO_2$, 5% $O_2$ and 90% $N_2$ or 5% $CO_2$ in air).

Following culture in suspension for up to 11 days, embryoid bodies are dispensed by mechanical or chemical means and can be allowed to reattach to tissue culture plates treated with gelatin or matrix, in ES medium. Displaced, plated embryoid bodies will form flattened monolayers and can be maintained by replacing medium every 2 days.

Analysis of Embryoid Bodies and Differentiated Cells

We used immunofluorescent antibody staining up to 7 days after plating to confirm the existence of cells of the neural phenotype. Cells were fixed in 30% methanol/10% acetic acid before incubation with antibodies. Antibodies that were used are as follows: rabbit anti-bovine GFAP (DAKO), anti-Forse-1 (Developmental Studies Hybridoma Bank), anti-bovine MAP-2 (Roche), anti-human NCAM/CD56 (DAKO) and anti-O1 (provided by S.-C. Zhang, University of Wisconsin). All primary antibodies are mouse monoclonals except anti-GFAP. Secondary antibodies, FITC-conjugated goat anti-mouse IgG and biotin-conjugated goat anti-rabbit, as well as AMCA-conjugated streptavidin were purchased from Jackson ImmunoResearch.

The Forse-1 antibody recognizes phosphacan, a brain-specific chondroitin sulfate proteoglycan that binds neural cell adhesion molecules in the embryonic CNS of both humans and rodents. K. Allendorfer et al., 6 Mol. And Cell. Neuro. 381–395 (1995); S. Tole et al., 15 J. Neuro. 957–969 (1995). The O1 antibody identifies pro-oligodendrocytes present from day 3 in embryonic mouse brain cultures. M. Schachner et al., 83 Dev. Biol. 328–338 (1981); I. Sommer, et al., 83 Dev. Biol. 311–327 (1981).

Within three days of plating, the neural precursors, stained by Forse-1 and O1, were observed. The Forse-1 antibody stained numerous rounded cells, whereas very sparse, flattened cells with extensive projections were stained with the anti-O1 antibody.

Neurons and glial were detected, 3 days and later after plating, by positive staining of neural cell adhesion molecule (NCAM)/CD56 (FIG. 3), microtubule-associated protein-2 (MAP-2)(FIG. 3), βIII-tubulin and glial fibrillary acidic protein (GFAP). NCAM is a cell adhesion molecule thought to be important in cell-cell interactions within the neuroepithelium. B. Cunningham, et al., 236 Science 799–806 (1987); J. Ritz, et al., 42 Adv. Immuno. 181–211 (1988). MAP-2 plays an important role in brain microtubule assembly. βIII-tubulin is a neuron-specific marker, and glial fibrillary acidic protein (GFAP) is an astrocyte marker.

Differentiation into Lineages

Embryoid bodies can be differentiated into a variety of desired lineages. For example the embryoid bodies could be used to derive hematopoietic cells using techniques analogous to those used for mouse in M. Wiles et al. 111 Development 259–267 (1991). In this regard one could plate the embryoid bodies in serum-containing medium in the presence of 2 i.u./ml erythropoietin or IL-3.

If cardiac lineages are desired one could use techniques analogous to T. Doetschman et al., 87 J. Embry. Exper. Morph. 27–45 (1985). One could plate the bodies in serum-containing medium with no additives.

To develop neural lineages one could plate the embryoid bodies in the presence of 20 ng/ml fibroblast growth factor plus 20 ng/ml epidermal growth factor. This is analogous to techniques described in B. Reynolds et al., 255 Science 5052 (1992).

The present invention thus provides an effective method for making primate embryoid bodies from primate ES cells. While the above work was focused on rhesus and human embryonic stem cells (and neural cells derived therefrom via these embryoid bodies), the techniques described herein should work broadly for primate embryonic stem cells and other cell types. Further, while specific techniques for clump removal have been discussed, the invention is not limited to those alone. Rather, other techniques for removing the cells in clumps from the substrate should work.

Thus, the invention is not limited to the specific embodiments described herein. Rather, the claim should be looked to in order to judge the full scope of the invention.

INDUSTRIAL APPLICABILITY

The present invention provides a supply of human and other primate embryoid bodies suitable for research, medical purposes, and differentiation into lineages.

We claim:

1. A method for producing differentiated human cells from human embryonic stem cells, the method comprising:
   culturing human embryonic stem cells under conditions such that at least some of the cells adhere to a substrate;
   removing the adhering colonies of the embryonic stem cells from the substrate in clumps;
   then incubating the clumps in a container under conditions in which the clumps are essentially inhibited from attaching to the container and under conditions in which the clumps of embryonic stem cells coalesce into embryoid bodies; and
   culturing the embryoid bodies to produce human differentiated cells.

2. The method of claim 1, wherein the human differentiated cells are selected from the group consisting of neural cells, cardiac cells and hematopoietic cells.

3. The method of claim 1, wherein the removal step is conducted in the presence of an enzyme that promotes disassociation of the clumps as clumps from the substrate.

4. The method of claim 3, wherein the enzyme is dispase.

5. The method of claim 1, wherein the removal step is conducted in the presence of a chelating agent.

6. The method of claim 1, wherein the removal step comprises mechanically scraping the clumps from the substrate.

7. The method of claim 1, wherein the removal step is conducted in the presence of trypsin, calcium and magnesium.

8. The method of claim 1, wherein the incubation step comprises agitating the container.

9. The method of claim 1, wherein the incubation step is conducted in a container made of plastic.

10. The method of claim 1, wherein the incubation step is conducted in the presence of a serum-free medium.

* * * * *